(12) United States Patent
Rabbett

(10) Patent No.: US 9,151,729 B2
(45) Date of Patent: Oct. 6, 2015

(54) CARBON MONOXIDE SENSOR SYSTEM

(75) Inventor: Michael David Rabbett, Chicago, IL (US)

(73) Assignee: BRK Brands, Inc., Aurora, IL (US)

( * ) Notice: Subject to any disclaimer, the term of this patent is extended or adjusted under 35 U.S.C. 154(b) by 446 days.

(21) Appl. No.: 13/606,321

(22) Filed: Sep. 7, 2012

(65) Prior Publication Data

US 2013/0062223 A1 Mar. 14, 2013

Related U.S. Application Data

(60) Provisional application No. 61/532,365, filed on Sep. 8, 2011.

(51) Int. Cl.
*G01N 27/407* (2006.01)
*G01N 27/404* (2006.01)

(52) U.S. Cl.
CPC ........ *G01N 27/4074* (2013.01); *G01N 27/4045* (2013.01); *Y10T 29/49007* (2015.01)

(58) Field of Classification Search
CPC ... G01N 27/304; G01N 27/31; G01N 27/406; G01N 27/407; G01N 27/4071; G01N 27/7072; G01N 27/4073; G01N 27/4074
See application file for complete search history.

(56) References Cited

U.S. PATENT DOCUMENTS

| | | | |
|---|---|---|---|
| 6,948,352 B2 | 9/2005 | Rabbett et al. | |
| 7,378,008 B2 | 5/2008 | Inoue et al. | |
| 7,404,882 B2 | 7/2008 | Prohaska et al. | |
| 7,435,321 B2 | 10/2008 | Inoue et al. | |
| 7,582,196 B2 | 9/2009 | Babes-Dornea et al. | |
| 7,601,250 B2 | 10/2009 | Prohaska et al. | |
| 2004/0134780 A1* | 7/2004 | Inoue et al. | 204/424 |
| 2006/0237333 A1 | 10/2006 | Planje | |
| 2008/0041730 A1* | 2/2008 | Caro et al. | 205/555 |
| 2008/0289962 A1 | 11/2008 | Prohaska et al. | |
| 2010/0170795 A1 | 7/2010 | Cowburn et al. | |

FOREIGN PATENT DOCUMENTS

EP 0990895 4/2000
JP 2000111519 A 4/2000

* cited by examiner

*Primary Examiner* — J. Christopher Ball
(74) *Attorney, Agent, or Firm* — Lawrence J. Shurupoff

(57) ABSTRACT

A gas sensor having first and second electrodes, an ion conducting solid electrolyte membrane positioned therebetween, first and second electrically conductive gas diffusion layers, first and second electrode contact members for electrically coupling said first and second electrodes to an external circuit, a water reservoir, a gas entry passageway and a water permeation barrier for controlling the transport of water vapor to the ion conducting solid electrolyte membrane. The water permeation barrier is a thin walled member which allows water vapor to diffuse therethrough and evaporate from an exit surface, the thickness of the water permeation barrier controlling the internal relative humidity of the sensor. A method for adjusting the present sensor in-situ due to changes in the current humidity conditions of the sensor so as to keep the gas sensitivity loss within a predetermined range is also disclosed.

24 Claims, 4 Drawing Sheets

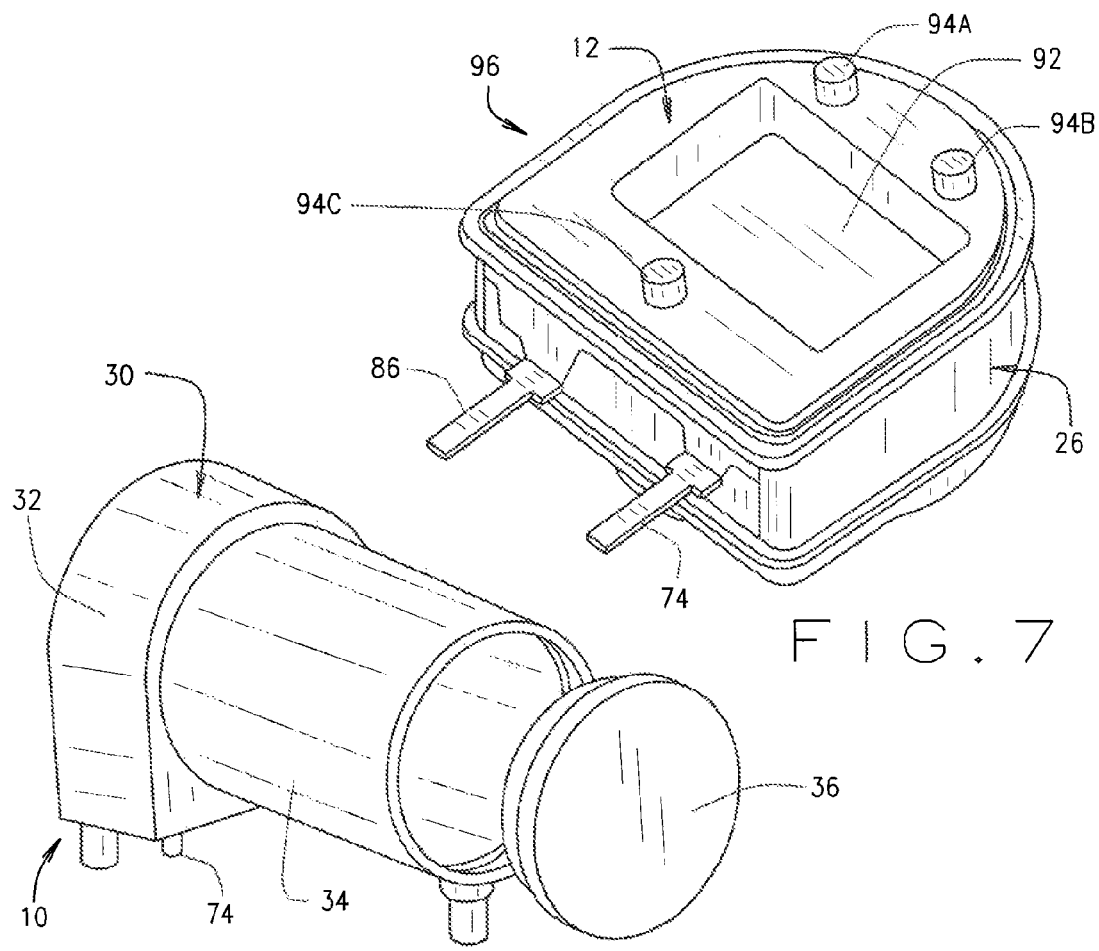
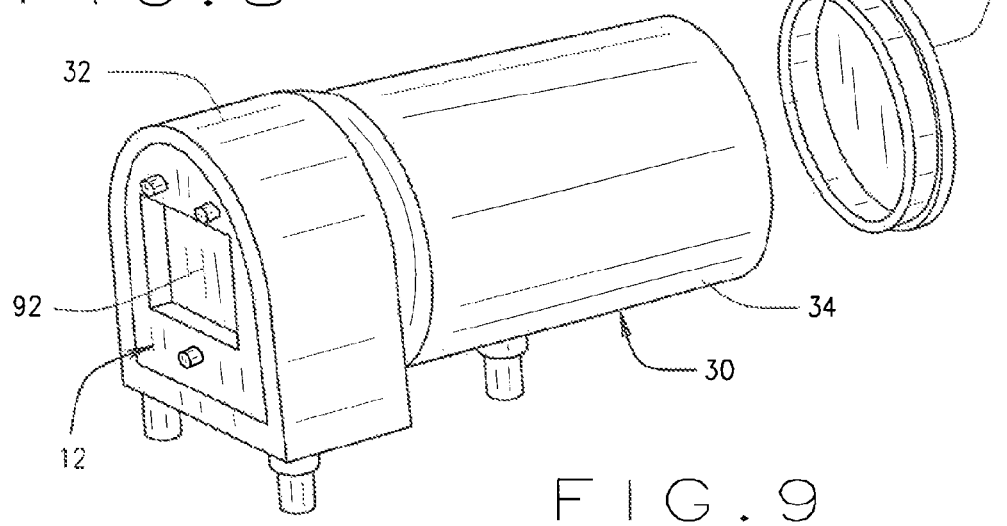

CARBON MONOXIDE SENSOR SYSTEM

CROSS-REFERENCE TO RELATED APPLICATION

This application claims the benefit of and priority to U.S. Provisional Patent Application Ser. No. 61/532,365, filed Sep. 8, 2011, entitled CARBON MONOXIDE SENSOR SYSTEM, which application is hereby incorporated by reference to the extent permitted by law.

BACKGROUND OF INVENTION

The present invention relates generally to an electrochemical sensor for the detection of carbon monoxide and, more particularly, to the construction, operation and method of manufacturing a carbon monoxide sensor having a gas diffusion capillary transport construction for controlling the gas entry to the sensor, a water permeation barrier for controlling the transport of water vapor from the water reservoir to the main sensor cell, and a method of compensation for changes in sensor CO sensitivity caused by humidity changes.

Electrochemical sensors for toxic and combustible gases sense the presence of the target gas by either an electrochemical oxidation or reduction process at a catalytic electrode surface. This process either liberates (oxidation) or consumes (reduction) electrons which are supplied to the electrode by the measurement circuit. The current represented by this flow of electrons is the output of the sensor and it is directly proportional to the number of target gas molecules reacting at the electrode.

The electrode (where the target gas reacts) is generally referred to as the "working electrode" and it is partnered with a second electrode which is not exposed to the target gas. The second electrode is generally referred to as the "counter electrode" and it is separated from the working electrode by a material that will support the flow of chemical ions, but will not support the flow of electrons, namely, an ion conducting material. The counter electrode is also connected to the measurement circuit and undergoes electrochemical reactions so as to balance the current associated with the working electrode.

The ion conducting material is referred to as the "electrolyte" and typical examples include sulphuric acid and salt water. The electrochemical reaction at the working electrode also produces ions, in addition to the production/consumption of electrons, and these ions diffuse through the electrolyte to the counter electrode. Here they consume/liberate electrons to balance the charge flow in the system and ensure that there is no net accumulation of charge on either electrode.

The rate of electrochemical reaction can be controlled by the voltage differential between the working electrode and the electrolyte, so sometimes a third electrode is added to the structure (referred to as the "reference electrode") to help control this potential. However, the design of sensors used in most carbon monoxide (CO) detectors for residential use is a two (2) electrode sensor with just working and counter electrodes.

Although there are many types of ion conduction mediums, only a few function well at room temperature. The first group of electrolytes are based on ion containing liquids (often aqueous but not always) such as acids or salt solutions. The second group are the ion conducting plastics which is epitomized by the material sold under the trademark NAFION, produced by DuPont.

The sensors mentioned above all require the presence of water in the electrolyte in order to function and there are two strategies to ensure its presence.

The first strategy, which works well with sensors based on mineral acids such as sulphuric acid, relies on the hygroscopic nature of a concentrated acid to draw water into the sensor when the external atmosphere is humid. In contrast, when the external atmosphere is dry, the electrolyte will lose water, increasing the concentration of the acid. The reduction in water content of the acid reduces the water vapor pressure above the acid and at some point this comes into equilibrium with the water vapor pressure in the surrounding atmosphere. When equilibrium is reached the electrolyte stops loosing eater and provided that the atmosphere is not completely dry, the electrolyte retains sufficient water to function. However, as the atmospheric humidity swings up and down, the strength of the acid in the electrolyte changes and in extreme cases of high humidity, the increasing volume of the electrolyte (caused by water absorption) can cause the sensor to burst. In addition to these problems, acid based sensors require the use of noble metal internal parts (such as gold or platinum wires) making them expensive and there are always corrosion problems.

The second strategy does not rely on atmospheric moisture to replenish the water in the electrolyte. Instead, the sensor incorporates a water reservoir to keep the electrolyte in good working condition. Water is continually lost from this reservoir to the outside atmosphere through the gas entry hole (the hole through which the target gas can get from outside the sensor to the working electrode) and it is usually this loss of water that limits the lifespan of this type of sensor. However, provided the entry hole is small, the water vapor pressure inside the sensor is almost constant, providing constant and repeatable water content for the electrolyte.

It is therefore desirable to provide a carbon monoxide sensor which can improve the lifespan of the sensor by controlling the gas entry to the sensor, by controlling the relative humidity inside the sensor, and by compensating for changes in sensor CO sensitivity due to humidity changes.

SUMMARY OF THE INVENTION

The present CO sensor is specifically designed for detecting and generating a warning with respect to a dangerous condition such as the presence of carbon monoxide (CO). In general, electrical chemical sensors employ a chemical reaction to convert CO to carbon dioxide ($CO_2$) to create a chemical imbalance in a portion of the sensor's cell which in turn generates a current indicative of the amount of CO present.

The present CO sensor construction includes an ion conducting solid electrolyte membrane positioned between a working electrode and a counter electrode. This structure including the electrolyte membrane and its associated electrodes (electrode/electrolyte structure) is generally referred to as the membrane electrode assembly (MEA). This assembly normally refers to a polymer electrolyte membrane with the working and counter electrodes deposited directly upon the membrane. These membranes are commercially available such as those supplied by DuPont under the trademark NAFION 117, PALL RAI's R4010 or those supplied by Dow under the trademark XUS-1304. The NAFION electrolyte includes platinum/carbon electrodes (working and counter) deposited directly onto the solid membrane. The MEA allows the passage of ions between the working electrode and the counter electrode without allowing the passage of either the target gas, or electrons. The working electrode electrochemically oxidizes or reduces the target gas thereby resulting in the emission or absorption of both electrons and ions. The counter electrode completes the electrochemical conversion of the target gas.

More specifically, when a toxic gas such as CO is introduced from an external environment to the working electrode, an oxidation reaction occurs at the working electrode where CO is oxidized into carbon dioxide, and protons and electrons are generated by the reaction. The protons which are ions of hydrogen migrate across the solid electrolyte membrane to the counter electrode where they react with electrons and oxygen to form water in a reduction reaction. This electrochemical reaction generates an electrical signal between the electrodes in response to the presence of the toxic gas, which signal is proportional to the rate of oxidation of CO molecules at the working electrode. This electrical signal can be measured by detector circuitry to determine the gas concentration.

The present sensor construction likewise includes a pair of gas diffusion layers (GDL) positioned on each opposite side of the MEA. The MEA is sandwiched between a top and a bottom GDL and, as will be hereinafter explained, the GDLs are sandwiched between top and bottom electrode contact plates made of a base metal such as brass and this entire structure makes up the core of the present sensor. In front of the top working electrode contact plate is a structure for controlling gas entry into the sensor (the gas diffusion barrier) and behind the bottom counter electrode contact plate is a structure to control water entry from a water reservoir (the permeation barrier).

More specifically, the GDLs are in contact with the respective working and counter electrodes of the MEA and are gas porous and electrically conductive. The GDLs are not hydrophobic since they each include an opening extending centrally therethrough. At least a $1/16^{th}$ inch diameter hole is punched through each GDL layer in alignment with the entrance aperture to allow the target gas to enter the sensor. The size and tortuosity of the entrance aperture is adjusted to limit the rate at which the target gas can enter the sensor to effectively control the CO sensitivity of the sensor. A groove associated with the front compression plate member defines part of the entry aperture.

The GDLs are both made of an electronically conducting porous material and since each GDL is only approximately 0.01 inches thick, the $1/16^{th}$ inch diameter hole (0.062 inch diameter) extending through each GDL will allow water, water vapor or any other gas to pass therethrough. Even if the GDLs are made out of a hydrophobic material, the presence of the hole extending through each GDL renders such layers non-hydrophobic, that is, water from the external environment can pass through the entry opening and through the hole in the top GDL to the working electrode. By being electrically conductive and in direct contact with the working electrode, the top GDL electrically connects the working electrode with the top electrode contact plate which in turn connects the sensor to an appropriate measuring device.

The bottom GDL which likewise includes at least a $1/16^{th}$ inch diameter hole punched therethrough is positioned adjacent to and in direct contact with the counter electrode of the MEA. A conductive silicone rubber member is positioned in direct contact with both the bottom GDL and the bottom electrode contact plate. Like the top GDL, the bottom GDL likewise protects the counter electrode from exposure to liquid water from the water reservoir as will be hereinafter further explained, except for the opening extending centrally therethrough. The electrically conductive bottom GDL is positioned between the counter electrode and the conductive silicone rubber member. A central opening exists in the conductive silicone rubber member such that water vapor from the water reservoir can pass through such opening and through the opening associated with the bottom GDL so as to reach both the counter and working electrodes as well as the solid electrolyte membrane therebetween thereby providing relative humidity to the entire MEA. By being electrically conductive and in direct contact with the counter electrode, the bottom GDL as well as the conductive silicone rubber member electrically connect the counter electrode with the bottom electrode contact plate which in turn electrically connects the counter electrode with an appropriate measuring device.

The entire sensor construction is positioned between a top compression plate member and a bottom compression plate member and may include other possible rubber seals, gaskets, shims and spacer members therebetween. It is also recognized that some of the spacer/shim/seal members can be eliminated and/or can be integrated into unitary members.

The rear compression plate member includes a substantially thin wall which extends across the water reservoir and forms the permeation barrier of the present sensor. This permeation barrier has a controlled thickness and diameter. The rear compression member is mateable with the water reservoir portion of the overall sensor assembly which contains a sufficient quantity of liquid water or other aqueous liquid. A reinforcement disc or plug rests on a shoulder or annular flange surrounding the permeation barrier and protects the thin wall barrier from compression forces. The only barrier between the water reservoir and the opening extending through the reinforcement member is the substantially thin wall permeation barrier or film associated with the rear compression plate member which lies directly over the water reservoir. Liquid water is prevented from entering the main sensor cell configuration by this thin wall structure located within the annular flange associated with the rear compression member. Clearly, liquid water from the water reservoir cannot pass through this thin wall structure since it is solid and extends continuously and entirely across the water reservoir and the exit opening to the main sensor cell. On the other hand, since this thin wall structure is typically approximately 0.005 inches thick, water vapor from the water reservoir will be able to permeate through this thin wall structure so as to supply enough water vapor to the MEA to keep the sensor hydrated during its useful life.

A cap or cover seals the opposite end of the water reservoir and completes the overall sensor construction. The top and bottom contact plates are attached to an appropriate measuring device or controller/microprocessor for sounding an alarm based upon the levels of CO measured by the present sensor. Once the input electrical signal is received, an output signal can be directed to a display such as an LED display which can show the concentration of gas, or to an alarm device if the signal received from the sensor indicates a given critical level of CO measured. This alarm can be a buzzer, beeper, light or other indicating warning.

The overall structure of the present sensor assembly is a glass filled Vectran plastic which is much less expensive and more versatile than the stainless steel used by others. A further advantage of the plastic housing is that it is no longer necessary to use ultra pure water in the reservoir to avoid corrosion of the sensor housing. Moreover, plastic facilitates the method of constructing and sealing the present sensor as will be hereinafter further explained. Unlike most other sensor designs, the present sensor design will operate with a low internal humidity.

The lower internal humidity reduces the rate of water loss significantly (thus increasing lifespan or reducing the size of the sensor), but it does make the sensor sensitive to the external humidity. The effect is not large and can be compensated by making a simple electrical measurement of the sensor.

BRIEF DESCRIPTION OF THE DRAWINGS

For a better understanding of the present invention, reference may be made to the accompanying drawings.

FIG. 7 is a perspective view of the assembled MEA stack positioned between the front and rear compression plate members.

FIG. 8 is a perspective view of the fully assembled sensor assembly of FIG. 1 looking in the direction towards the water reservoir showing the water reservoir cover or cap in a removed position.

FIG. 9 is a perspective view of the fully assembled sensor assembly of FIG. 1 looking in the direction towards the front portion of the sensor assembly showing the water reservoir cover or cap in a removed position.

It should be understood that the drawings associated herewith are not necessarily to scale and that the embodiments disclosed herein are sometimes illustrated by fragmentary views. In certain instances, details which are not necessary for an understanding of the present invention or which render other details difficult to perceive may have been omitted. It should also be understood that the present invention is not necessarily limited to the particular embodiments illustrated herein.

DETAILED DESCRIPTION

Figure 1:
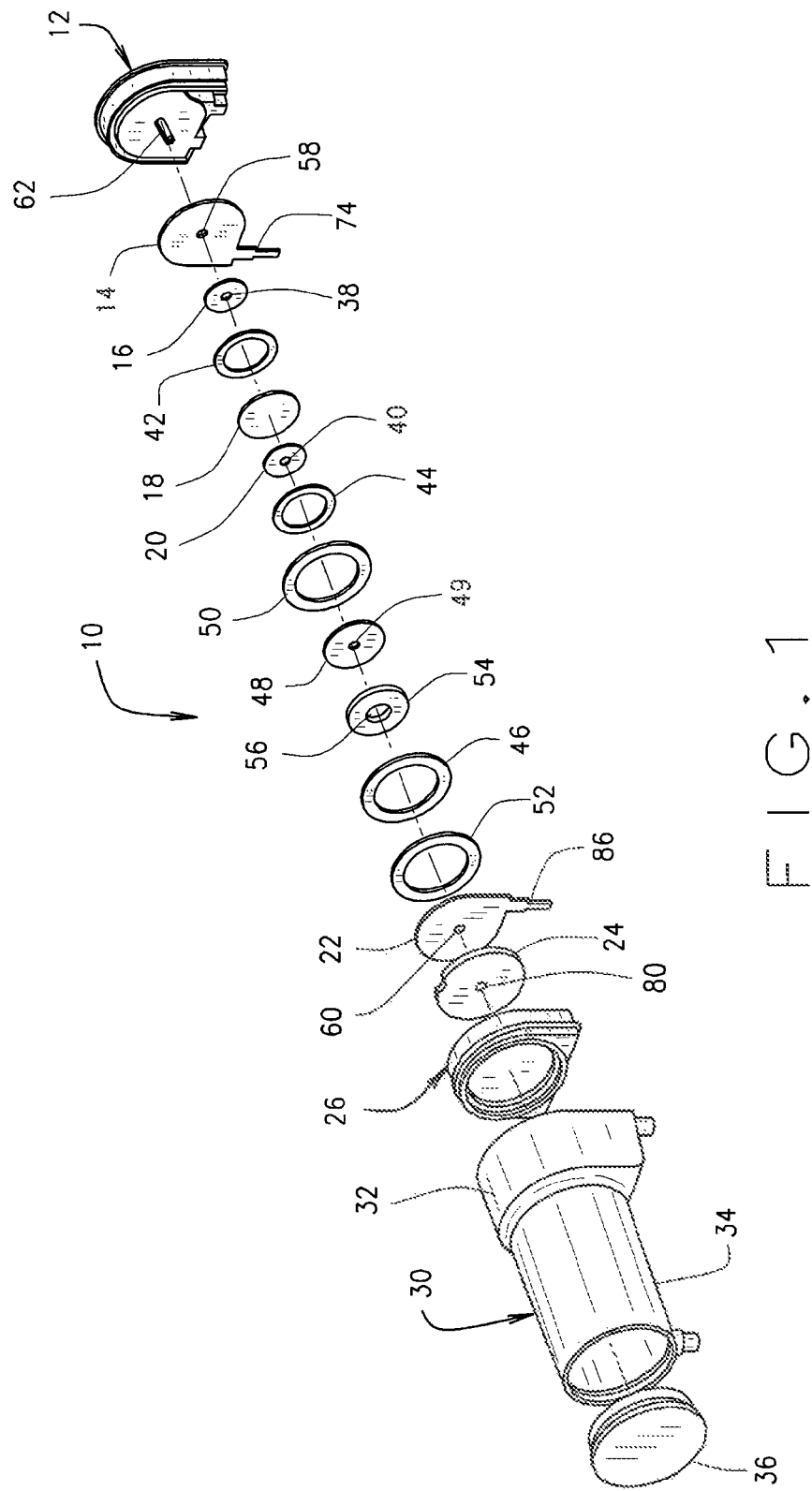
FIG. 1 is an exploded perspective view of the present CO sensor assembly constructed in accordance with the teachings of the present invention.
Figure 2:
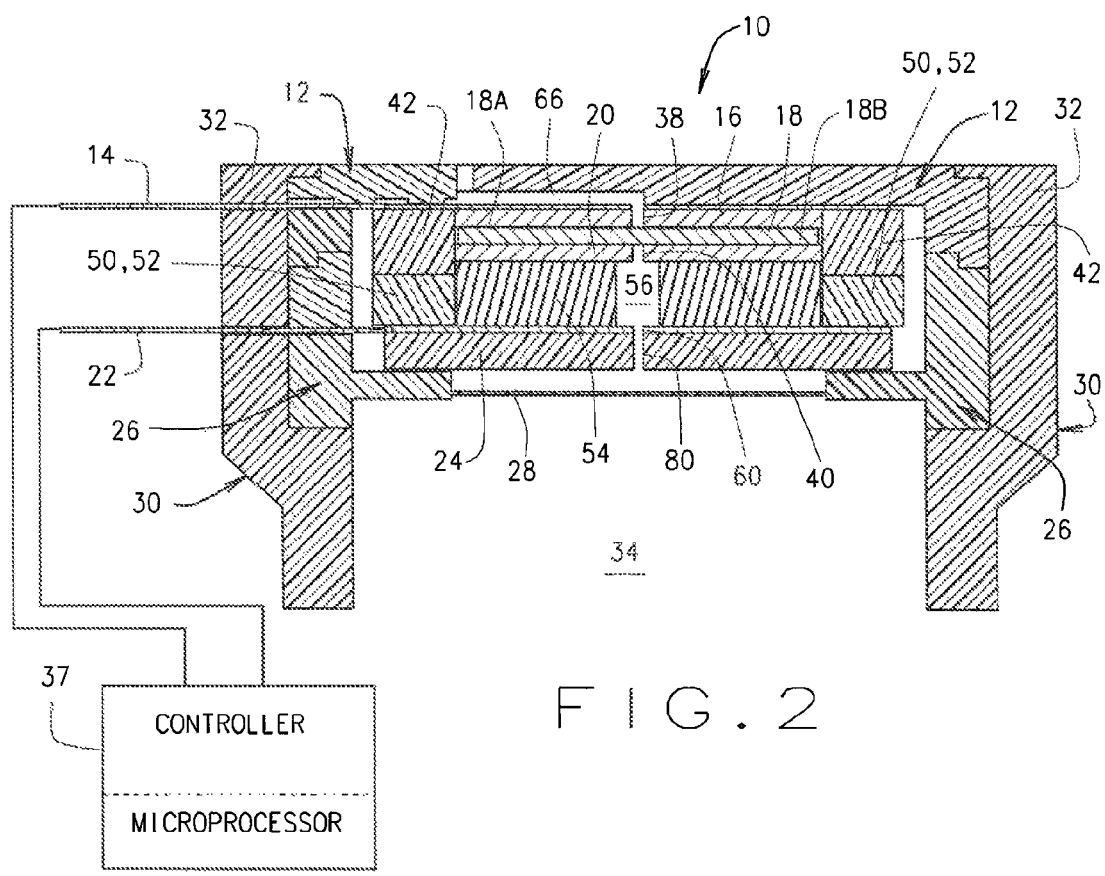
FIG. 2 is a partial cross-sectional view of the sensor assembly of FIG. 1.

Referring to the drawings by reference numbers wherein like numbers refer to like parts, the number 10 in FIGS. 1 and 2 identifies one embodiment of an electrochemical sensor for the detection of carbon monoxide constructed according to the teachings of the present invention. An exploded view of the present sensor 10 is illustrated in FIG. 1 and includes a top/front compression plate member or first housing member 12, a top/front electrode contact plate 14, a top or first gas diffusion layer (GDL) 16, an electrode/electrolyte structure generally referred to as a membrane electrode assembly (MEA) 18, a bottom or second GDL 20, a bottom/rear electrode contact plate 22, a reinforcement disc 24, a bottom/rear compression plate member or second housing member 26 housing a permeation barrier 28, an over-molded rear body 30 which includes a housing 32 for enclosing the internal sensor parts and a water reservoir 34, and a rear cover plate 36 for closing and sealing the water reservoir. The MEA 18, the pair of GDLs 16 and 20, and the top and bottom electrode contact plates 14 and 22 are surrounded by a series of spacers and sealing members as will be hereinafter further discussed for sealing of the sensor arrangement and alignment of the various component parts between the front and rear compression plate members 12 and 26.

FIG. 2 is a cross-sectional view of the present sensor 10 in its assembled form showing the relationship of the various component parts relative to each other and connected to a controller 37 incorporating a microprocessor for controlling the entire detector system. The MEA 18 is an important component of the present sensor construction and, in the embodiment illustrated in FIGS. 1 and 2, includes a thin NAFION membrane coated with electrodes on either side. NAFION is an anionically conducting polymer that does not conduct electrons. It functions as the electrolyte in the electrochemical sensor 10 and transports the hydrogen ions, liberated during the oxidation of carbon monoxide, from the front working electrode 18A to the rear counter electrode 18B. The electrodes 18A and 18B are composed of a porous but electrically continuous mixture of a carbon supported catalyst (platinum) and NAFION. Oxidation occurs at the three phase boundary of NAFION, platinum and a monolayer of water that coats the platinum. The electrode composition is >50% NAFION, <50% Platinum/carbon.

The MEA 18 is sandwiched by the two gas diffusion layers (GDLs) 16 and 20 which are composed of a porous graphite based conductive material. Since graphite does not bond to itself, manufacturers add a small amount of Teflon fluorocarbon (PTFE) to the mixture to obtain a viable material. The Teflon fluorocarbon addition renders the material very slightly hydrophobic so holes 38 and 40 are punched in the respective GDLs 16 and 20 to allow the passage of water vapor. Hole 38 extends completely through GDL 16 and hole 40 extends completely through GDL 20. The material used for the GDLs 16 and 20 is a commercial product designed to be used with an MEA in fuel cell assemblies. Its purpose in a sensor construction is twofold, firstly it provides electrical contact to the electrodes 18A and 18B of the MEA 18, and secondly it allows gases to spread out across the electrode surface.

As best illustrated in FIGS. 1 and 2, the top GDL 16 lies in direct contact with the top/front electrode contact plate 14. An annular silicone rubber spacer 42 is positioned adjacent both the top GDL 16 and the MBA 18 as best illustrated in FIG. 2. In between the bottom GDL 20 and the bottom/rear electrode contact plate 22 lies a plurality of spacers and sealing members including spacer members 44 and 46, a shim 48 with an opening 49 extending therethrough, silicone rubber gaskets or sealing members 50 and 52 and a conductive silicone rubber member 54, all of which component parts are illustrated in FIG. 1 and some of which are illustrated in FIG. 2. The main components of the present sensor 10 are assembled by stacking together all of the component parts between and including the top and bottom electrode contact plates 14 and 22 as illustrated in FIGS. 1 and 2. This assembled stack of component parts, referred to hereinafter as the MEA stack, is then compressed between the front compression or front housing plate member 12 and the reinforcement disc and rear compression plate members 24 and 26 as will be hereinafter further explained. When fully assembled, the MEA stack is under significant compression so the conductive silicone rubber member 54 is included in the compressed components to provide some resilience and to allow for thermal expansion and contraction during thermal cycling. The conductive silicone rubber member 54 likewise includes a hole or opening 56 extending completely therethrough to allow for the passage of water vapor into the active parts of the sensor as will be hereinafter further explained.

A compression force is applied to the MEA stack components through the top and bottom electrode contact plates 14 and 22 which are made of simple brass with a thickness of approximately 0.005 inch. Each contact plate has a 1 mm hole at its center, the hole 58 in the front contact plate 14 allowing any CO to access the active components of the sensor while the hole 60 in the rear contact plate 22 allowing water vapor from the reservoir 34 to also access the active components. The size of the holes 58 and 60 is not critical to the functioning of the sensor.

Figure 3:
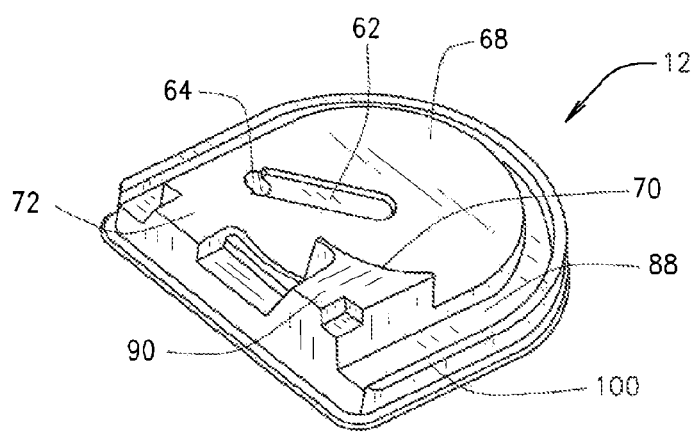
FIG. 3 is a perspective view of the front compression plate member illustrated in FIG. 1.

When assembled, the top/front contact plate 14 is forced against the rear surface of the front compression member 12 which is made of Vectran. There is a groove 62 molded into the rear surface of the front compression member 12 as best illustrated in FIG. 3 which, in combination with the front electrode contact plate 14 (FIG. 4), forms the gas limiting diffusion aperture or passageway 66 as described below. The front portion of front compression plate 12 includes a recess 92 (FIG. 7) designed to hold an activated carbon filter for suppression of sensitivity to organic vapors and to protect the sensor from poisoning as will be hereinafter further explained.

The bottom/rear electrode contact plate 22 is forced against the reinforcing disc 24 which is likewise made of Vectran and designed to protect the diaphragm or permeation barrier 28 associated with the rear compression member 26. The diaphragm or permeation barrier 28 is made of a polycarbonate plastic material sold under the trademark MAKROLON, or other similar material, and it has a center diaphragm section that is of a controlled thickness and diameter, typically in the neighborhood of about 0.012 inches thick. This barrier 28 prevents the access of liquid water to the electrodes 18A and 18B from the reservoir 34, but it does allow the passage of water vapor by the process of permeation as will be hereinafter further explained.

Full compression of the MEA stack is achieved when the two outermost compression members or housing members 12 and 26 are engaged, this assembly, assembly 96 in FIG. 7, is then over-molded with a Vectran body 30 which holds the compressed MEA stack together and also forms the body for the water reservoir 34. Water vapor from the reservoir 34 passes through the permeation barrier 28 to keep the active components of the sensor humidified as will be hereinafter explained. The reservoir 34 is then filled and closed with a Vectran cap or cover 36 which is sealed to the reservoir by either welding (spin or ultrasonic) or by adhesive. The choice of polymer for the over-molded body 30 is critical as it must be both mechanically strong and it must have a very low water permeation rate. Glass filled Vectran fulfills both of these requirements.

One of the primary requirements for a good gas sensor, that will be stable over a wide range of environmental conditions, is that the sensor should be diffusion limited. This means that the output from the sensor is determined solely by the rate at which the target gas can diffuse into the sensor and not by any other rate limiting processes within the sensor, such as the rates of chemical reactions. In order to achieve diffusion limiting over the full operating temperature range of the sensor it is necessary to force the target gas to diffuse through a limiting aperture or capillary. The rate or mass of gas transport through a capillary (or long narrow tube) is proportional to the cross-sectional area of the aperture divided by its length, that is, the gas transport rate can be reduced by reducing the area of the capillary aperture or increasing its length.

The conventional method for manufacturing a capillary is either to drill a hole mechanically through the thickness of the front compression plate 12 or to mold the hole or channel during the manufacture of the sensor casing. Unfortunately the dimensions of the capillary suitable for use with a CO sensor typically require a cross-sectional area of about 0.06 mm$^2$ combined with a length of a few millimeters.

Although it is possible to obtain drills of the required dimensions, they are very fragile and not suitable for a mass production environment. The only real possibility for drilling such a small hole is to drill it using a high power laser. However, laser drilled holes are rarely well controlled and are often conical rather than cylindrical, particularly when drilling deep holes. In addition, laser machining is a costly process, both in terms of capital equipment and also in consumables.

The aspect ratio of the capillary makes it almost impossible to mold such a hole or capillary directly as the mold tool would need to include a pin of the specific cross-section and length of the capillary. This pin would prove to be very fragile in use and it is likely that it would be impossible to eject the molded part without snapping the pin.

The present invention overcomes this problem by not attempting to mold the gas entry hole directly, but by molding a groove of the required dimensions first and then capping the groove with a flat surface to form a rectangular or triangular or other shaped channel or passageway with the required cross-section and length. This construction is illustrated in FIGS. 3 and 4.

More particularly, FIG. 3 shows the front compression plate or housing member 12 of sensor 10 as viewed from the inside of the sensor 10 as depicted in FIG. 1, with the molded groove 62 exaggerated in size for clarity. Gas enters the sensor through the hole 64 located at the left hand end of the groove 62, which hole has a diameter of typically about 1 mm and extends completely through to the front surface of the front compression plate 12. The channel 62 runs in the plane of the front plate 12 rather than through its thickness and this potentially permits a much longer diffusion control channel to be used.

Molding a groove, such as groove 62, with a depth of about 0.25 mm and a width of about 0.25 mm, is comparatively simple since it only requires a small ridge on the face of the molding tool. There is also no longer any limitation on the length of the channel caused by practical limitations of molding. That is, the tooling is no more likely to stick for a groove having a length of 25 mm than it is for a groove having a length of 1 mm.

Figure 4:
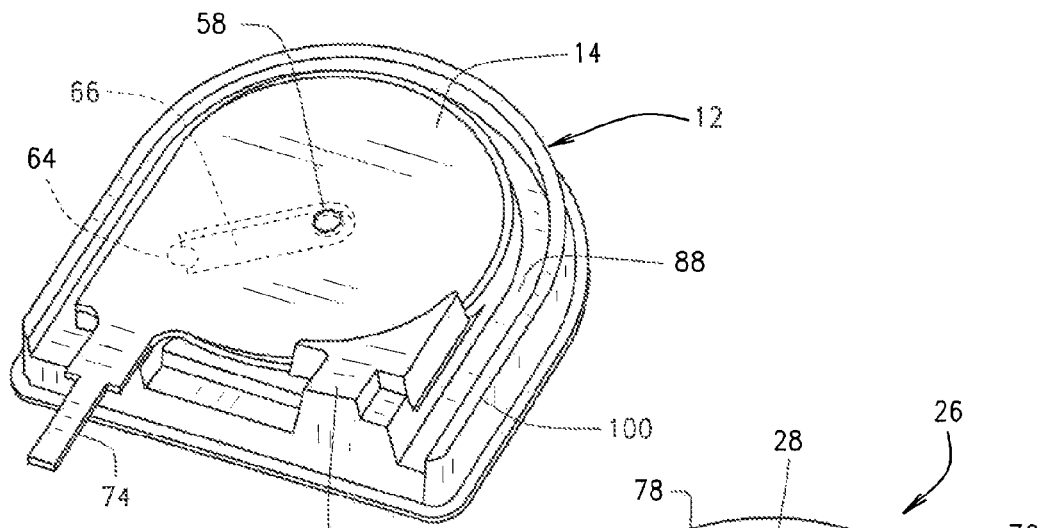
FIG. 4 is a perspective view of the front compression plate member of FIG. 1 with the top/front electrode contact plate positioned therein.

Closure of the groove 62 to form a channel or passageway 66 is accomplished by mating the front electrode contact plate 14 with the front compression plate member 12 as shown in FIG. 4. In this regard, the front housing compression plate member 12 includes a surface 68 (FIG. 3) for mating with the contact plate 14 and shoulder 70 forms an abutting surface for holding the contact plate 14 in proper position. The contact plate 14 is made from brass and confines the gas entering the sensor 10 to diffuse along the channel 66 until it reaches the exit hole 58 at the center of contact plate 14 from whence it passes through the hole 38 associated with the top GDL 16 to the working electrode 18A of the sensors 10.

The "seal" between the brass contact plate 14 and the Vectran (glass filled) front compression plate 12 is ensured due to the large force applied to the back of the contact plate 14 from the remaining downstream active parts of the sensor as will be hereinafter further explained. In addition, the surface 68 of the front compression member 12 likewise includes an extension portion 72 (FIG. 3) for providing support to contact extension portion 74 of contact plate 14 for extending beyond the perimeter of front compression member 12 as best illustrated in FIG. 4. The contact extension portion 74 forms one of the electrical contact portions of the sensor for electrically connecting the present sensor 10 to an external circuit and/or to the controller 37. A smooth finish is specified for the surface portion 68 of the front compression member 12 and the perimeter of the front contact plate member 14 is sealed to the front compression member 12 by the over-molded body 30 of the sensor as will be hereinafter further explained. Gas entry to the present sensor 10 is controlled by the diffusion channel 66 constructed in the above-referenced manner.

Although the groove 62 has been described as being closed by mating the front electrode contact plate 14 to the surface 68 to form the gas entry passageway 66, it is recognized and anticipated that any member other than the electrode contact plate 14 can be used to close the groove 62 so long as this other member likewise includes an opening extending therethrough in communication with the groove 62 to provide an exit opening for the gas passing through the passageway 66. This other member could be an additional member positioned between the front electrode contact plate 14 and the front compression plate or housing member 12.

In order for the sensor 10 to function for an extended period, it is essential that the MEA 18 remains humidified and this is achieved by the transport of water vapor from the water reservoir 34. The water must be transported in vapor phase to avoid sudden shifts in the MEA equilibrium and/or potential poisoning of the MEA caused by the introduction of possibly contaminated liquid water.

The rate at which the MEA 18 loses water (assuming constant external relative humidity) is set by the properties of the gas entrance channel 66, that is, the water loss rate scales linearly with the gas sensitivity of the sensor. More accurately, the rate of loss of water is set by the transport properties of the gas diffusion barrier and the difference in humidity between the inside and outside of the sensor. Likewise the rate of transport of water from the reservoir 34 is determined by the properties of the interface between the MEA 18 and the water reservoir 34 and the difference in humidity between the two regions. The humidity inside the reservoir 34 is effectively 100% relative humidity (RH) and the humidity within the MEA 18 adjusts to balance the two transport rates. It is usual for the transport properties of the link from the reservoir 34 to be made a few times more efficient than those of the diffusion barrier, which ensures that the humidity inside the sensor remains in the range of typically about 75% RH to about 100% RH.

The problem in this case is making a simple efficient method of ensuring that water vapor, and not liquid water or other contaminants, has a path for transport from the water reservoir 34 to the MEA 18. The conventional method for controlling the transport of water vapor from the reservoir into the sensor is to use an aperture in the wall separating the two regions. This is simple, but it does have several disadvantages, namely, (1) the reservoir must be sealed during gas testing to prevent gas access to the rear counter electrode 18B, (2) the MEA 18 is exposed to any contaminants that are present in the water reservoir 34 so this precludes the use of some antifreezes to prevent the reservoir from freezing, and (3) a hydrophobic barrier has to be incorporated in the sensor to prevent the transport of liquid water into the sensor. This entails extra components including extra sealing gaskets to ensure that liquid water cannot pass the hydrophobic barrier, yielding yet more potential failure mechanisms for the sensor.

The conventional control solution to this problem relies on gas diffusion through a hydrophobic layer. However, there is a second process by which vapors may pass through a barrier, namely, via permeation. Permeability is generally taken to mean that material A is permeable to material B if material B can pass through material A under some form of concentration gradient in material B. There are two ways in which material A may be permeable; (1) it may be either micro or macro porous (e.g. like an open-cell sponge), or (2) the permeability may come about because material B can dissolve in material A, diffuse through material A, and then be evaporated from the far surface.

Materials that conform to the first process of permeability have no selectivity, that is, the permeability for all vapors is similar. Examples of permeable materials include the hydrophobic filters and gas diffusion layers in the known conventional sensors, electrode backing used in most gas sensors, building materials, rocks in underground fluid reservoirs, and a wide variety of other things.

Materials where the permeability is defined by the second process are more correctly referred to as semi-permeable materials because the step where the penetrant material dissolves into the semi-permeable material is usually chemically selective, that is, the permeability can be widely different for different penetrants. Semi-permeable materials include the material of the permeability barrier 28 in the present sensor 10, reverse osmosis membranes, some food packaging, dialysis tubing and other specialized applications where it is desired to separate materials.

The permeation barrier 28 in the present sensor is a solid film, without any holes or perforations, and the vapor passes through the barrier by first dissolving in the barrier material and then diffusing through the bulk of the barrier and evaporating from the exit face. Most materials are permeable to some extent, but plastics are particularly effective for this mode of transport. The second feature of permeation that is particularly applicable for use in a gas sensor is that this process is selective. In general, small molecules will permeate much faster than large molecules, but there is also a species specific aspect to the selectivity caused by the chemical sensitivity of the dissolution step. Particular plastics will have high permeation rates for molecules with which the plastic is compatible and much lower rates for other molecules. For instance it is possible to find a plastic for which the permeation rate for water is high and the carbon monoxide permeation rate is low. Permeation rates are also generally temperature sensitive, with the solution step having a negative temperature coefficient and the diffusion step having a positive coefficient. The exact temperature behavior of the permeation coefficient is a balance between these two effects and could be either positive, negative or neutral with respect to temperature, depending on the material.

The thin, walled permeability barrier 28 sensor is an integral part of the sensor 10 and the sensor will not function well without it. The present sensor 10 is specifically designed to reduce the water loss from the sensor which is achieved by choosing the specific material for the permeability barrier 28 for the following specific properties:

(1) the material is semi-permeable, not permeable, in that the permeability for water vapor is high and the permeability for other gases such as carbon monoxide, oxygen, and so forth is low; it is non-porous, hydrophilic and readily formable by injection molding;

(2) the material is chosen such that there is no significant variation of permeability with temperature, ensuring that the rate of passage of water depends only on the water vapor pressure difference across the barrier; and (3) the thickness of the barrier material is chosen so as to control the overall rate of water loss from the sensor.

Thus, by careful selection of the plastic material and selection of film thickness, it is possible to engineer a variety of temperature profiles for water transport while ensuring that the barrier is impervious to almost everything else. In particular, the use of polycarbonate, with a film thickness in the range of about 0.01 inches to about 0.03 inches has been found to provide good water transport, negligible carbon monoxide transport, negligible transport of organic vapors (such as from liquid antifreezes) and zero temperature coefficient.

Figure 5:
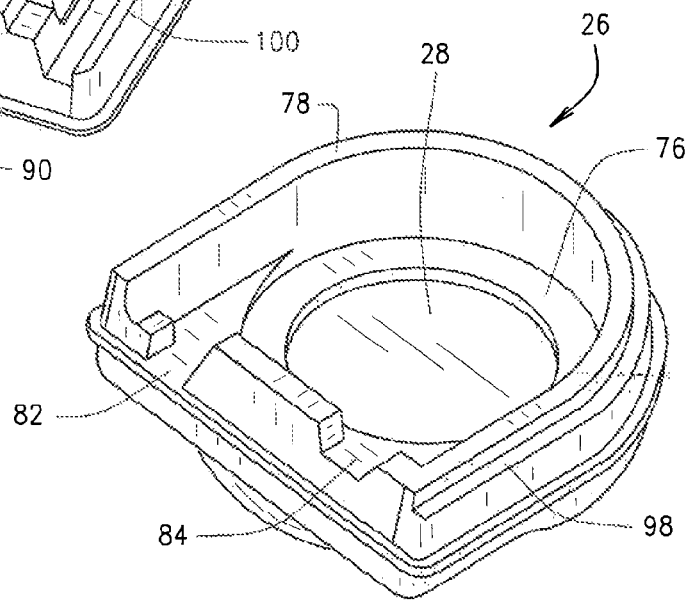
FIG. 5 is a perspective view of the rear compression plate member of FIG. 1.
Figure 6:
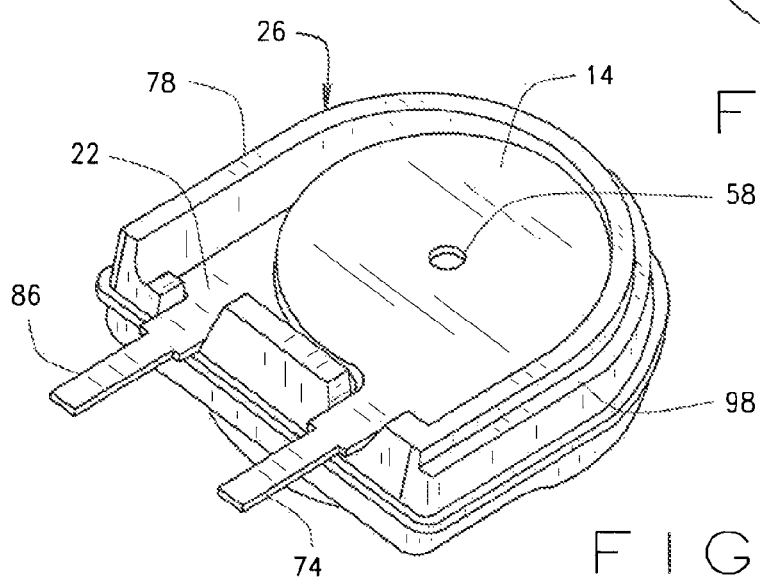
FIG. 6 is a perspective view of the rear compression plate member of FIG. 1 with the MEA stack positioned therein.

FIG. 5 shows the rear compression member 26 which is molded out of polycarbonate or some other suitable plastic. The circular region 28 in the center of member 26 forms the permeation barrier and has a controlled thickness. The reinforcement disk 24 rests on the shoulder 76 surrounding the permeation barrier 28 and protects the barrier from the compression forces generated by stacking the MEA stack within the rear compression member 26 and closing the same with the front compression member 12 as will be hereinafter further explained. The rear electrode contact plate 22 and the rest of the MEA stack are positioned within the recess formed by the annular wall portion 78 as best shown in FIG. 6. Water vapor from the water reservoir 34 will then pass through the permeation barrier 28, through the hole 80 (FIG. 2) in the center of the reinforcement disc 24, through the hole 60 (FIG. 2) in the rear electrode contact plate 22, and then into the MEA 18.

FIG. 6 illustrates the entire MEA stack positioned within the rear compression member or housing member 26. In this regard, rear compression member 26 includes a pair of slots 82 and 84 as illustrated in FIG. 5, slot 84 being elevated above slot 82. Slot 82 is positioned, sized and located so as to receive the contact extension portion 86 associated with the rear electrode contact plate 22 and slot 84 is positioned, sized and located so as to receive the contact extension portion 74 associated with the front electrode contact plate 14 as illustrated in FIG. 6. Like contact extension portion 74, contact extension portion 86 forms the other electrical contact portion of the sensor 10 for connecting to an external circuit and/or to the controller 37 as illustrated in FIG. 2. The rear electrode contact plate 22 forms the bottom of the MEA stack while the top or front electrode contact plate 14 forms the top of the MEA stack. The MEA 18 and its associated gas diffusion layers (GDLs) 16 and 20 are located within the recessed portion of the rear housing compression member 26 and within the annular flange portion 78 which provides secondary sealing means and protects the active parts of the MEA stack from the molded plastic during the over-molding process. Once the MEA stack is positioned within the rear housing compression plate member 26 as illustrated in FIG. 6, the front housing compression plate member 12 containing the gas diffusion groove 62 is next placed onto the MEA stack to form the gas diffusion barrier channel 66 as previously explained with respect to FIG. 4. In this regard, the front compression plate member 12 includes an annular groove or channel 88 adapted to receive the annular flange portion 78 associated with the rear compression plate member 26. Similarly, the front compression plate member 12 includes a raised step or flange portion 90 which is sized and shaped so as to be received within the slot 84 associated with the rear compression member 26 as illustrated in FIG. 5.

FIG. 7 illustrates the completed sub-assembly 96 of front and rear housing compression plate members 14 and 26, which sub-assembly houses the MEA stack therewithin as previously explained. In essence, the front compression member 14 forms a first housing member and the rear compression member 26 forms a second housing member of sub-assembly 96 for enclosing the MEA stack. A latch mechanism may be incorporated into the rear compression plate member 26 for holding the front and rear compression members 14 and 26 together after assembly. This latching mechanism would facilitate the transfer of the assembled unit 96 into a molding machine for the over-molding of the rear body 30 as will be hereinafter explained. The front surface of the front compression plate member 12 includes a recess 92 as best illustrated in FIG. 7 which is designed to house an activated carbon filter to reduce cross-sensitivity to organic solvents. The three projecting posts 94A, 94B and 94C illustrated in FIG. 7 are positioned and located so as to locate the cover of the activated carbon filter housing and will be heat stacked thereto. The extension portions 74 and 86 of the front and rear contact plates 14 and 22 extend through the bottom portion of the sub-assembly 96 illustrated in FIG. 7 for connecting to an external circuit such as the controller 37.

Sub-assembly 96 illustrated in FIG. 7 is now ready for placement into an injection molding machine and the entire sub-assembly 96 is over-molded thereby producing a continuous plastic body that ensures a good seal between the internal sensor parts and the external environment. The over-molded body 30 is made from glass filled Vectran, a liquid crystal polymer with a high melting point. The molding temperature is sufficient to partly melt the projecting rib 98 which extends around the perimeter of the rear compression member 26 to the flange 100 extending around the perimeter of the front compression member 12 to aid in sealing and to further improve the integrity of the seal between the over-molded body 30 and the sensor sub-assembly 96. Sill further, in addition to providing secondary sealing to the sensor sub-assembly 96, the over-molding process is extended behind the rear surface of the sensor sub-assembly 96 to provide the body for the water reservoir 34 as best shown in FIGS. 1, 8 and 9. The water reservoir 34 is closed with a simple cover or cap 36 that can be either welded or glued in position. As best illustrated in FIG. 2, when the over-molding process is completed, the over-molded body 30 includes a housing portion 32 which surrounds and encloses the side walls of sub-assembly 96 thereby forming one continuous exterior housing for the sensor 10. As stated earlier, because of the use of the permeation barrier 28 to separate the water reservoir 34 from the sensor assembly housed within sub-assembly 96, the present sensor is no longer sensitive to contaminants in the water reservoir 34.

FIG. 8 is a perspective view of the assembled sensor 10 looking in a direction towards the over-molded sensor body 30 with the water reservoir cap 36 removed while FIG. 9 is a perspective view of the assembled sensor 10 looking in a direction more towards the front portion of the sub-assembly 96 with the water reservoir cap 36 likewise removed. At least one end 74 of the electrical connecting extension portions 74, 86 associated with the front and rear electrode contact plates 14 and 22 can be seen projecting from the over-molded sensor body 30 in FIG. 8.

All of the structural component parts of the present sensor 10 are made of plastic. The plastic chosen is a high strength rigid glass filled liquid crystal polymer. Assembly and sealing of a plastic sensor is totally different than the assembly and sealing compared with the equivalent processes for a metal bodied sensor. More specifically, the issues of electrical contact to the active parts and sealing of a metal bodied sensor against the ambient environment are quite different.

Metal bodied sensors use the body of the sensor as the rear (usually counter electrode) contact and the surface containing the gas entrance aperture as the front (working electrode) contact. The active parts of the sensor are inserted into the open end of the sensor body and compressed between the body and the front contact. Sealing is typically achieved by crimping the projecting rim of the sensor body onto the outer surface of the front contact with an insulating spacer placed therebetween preventing electrical shorting of the sensor. The insulating spacer is also required to produce a gas tight seal between the two metal parts to prevent leaks.

The conventional method for assembling a plastic bodied electrochemical sensor is to first make the housing components, then assemble the sensor active parts and/or the electrolyte or water reservoir into one part of the housing and then finally to seal the parts of the housing together by welding or adhesive. This sealing process has proved to be one of the most problematic in the industrial production of plastic bodied gas sensors. Although ultrasonic welding is nominally the cleanest way to make this seal, in practice, it has often proved unreliable. The alternative, use of an adhesive, is difficult to automate and the adhesive used must be chemically compatible with the sensor materials as the internal parts of the sensor are exposed to the sealant.

In addition, electrical connection to the plastic sensor is typically made by one of two methods, either metal pins are inserted through the wall of the sensor body, a costly manual process that again can be the cause of leaks, or the case parts of the sensor incorporate conductive plastic components. There are problems with both of these solutions, namely, pin insertion has proved to be difficult to automate and plastics provide poor electrical conductivity compared to metals.

The assembly approach used in the present sensor design produces a significantly more rugged seal to the sensor parts and it is capable of mass production. The sensor structure of assembly 96 is essentially a stack of components punched from sheet materials and assembled into the assembly 96 using a pick-and-place machine or similar technology. Thus the entire assembly 96 of the sensor components housed therein can be automated. This saves time and money during the manufacturing and assembly stage and produces a much improved sensor assembly.

The permeability barrier 28 is an integral part of the present sensor structure and is also an integral part in the way that the present sensor 10 controls internal humidification. The MEA 18, within the sensor, experiences an internal humidity that is determined by the humidity external to the sensor and the ratio of transport coefficients between the input diffusion barrier ($T_{dif}$) and the permeability barrier ($T_{perm}$).

The mathematics behind this is fairly simple wherein RH refers to relative humidity:

$$\text{Internal RH}=(T_{perm}*100+T_{dif}*\text{External RH})/(T_{perm}+T_{dif}).$$

The rate of water loss from the sensor is a function of the internal RH and the transport coefficient of the input diffusion barrier ($T_{dif}$).

$$\text{Rate of water loss}=A*(\text{Internal RH}-\text{External RH})*T_{dif}.$$

where A is a simple constant for conventional sensors that use a hydrophobic membrane or an uncontrolled permeable membrane. The value of $T_{perm}$ is much higher than the value of $T_{dif}$ resulting in an internal RH level of above 90% and a rate of water loss that is determined entirely by $T_{dif}$. Given that the sensor CO sensitivity is also controlled by $T_{dif}$, the result is a fixed relationship between rate of water loss and sensor CO sensitivity.

However, for the present sensor design, the two transport properties can be adjusted independently. The sensor CO sensitivity is adjusted to the desired level and then the value of $T_{perm}$ is adjusted by changing the thickness of the permeability barrier so as to keep the internal RH above the target value for all external values of RH. The two transport parameters $T_{dif}$ and $T_{perm}$ increase as the ability of the respective barrier to transport water vapor increases.

The MEA is capable of working in a wide range of values of relative humidity and, provided that the RH is kept above 60%, the performance of the MEA is reasonably stable. Thus the present sensor is designed such that the value of $T_{perm}/T_{dif}$ is approximately 2.0. The result is that the rate of water loss from the present sensor is reduced by about 30% compared to that experience by a conventional sensor. The ability to reduce the rate of water loss has a major effect on the utility of the sensor in the real world. There is a continued demand for sensors with a longer lifespan, and given that the lifespan for this type of sensor is inversely proportional to the rate of water loss, the present sensor design is capable of producing a longer lived sensor for the same overall size, or it can produce a smaller sensor for the same lifespan.

A further advantage of using a semi-permeable material for the permeability barrier is that it is possible to operate the present sensor with the water reservoir 34 empty and unsealed. This is because the permeability barrier 28 is impervious to CO and no gas would able to enter the sensor 10 through an empty and unsealed water reservoir 34. The only entry of a gas into the sensor will still be through the gas entry channel or passageway 66. This capability has a major advantage in the logistics of sensor production because, for most sensors, the location of the sensor manufacture and sensor usage are different and often they are on different continents. The cost of transporting sensors from their point of manufacture to their point of usage is a significant part of the total cost of the sensor. This cost is usually dependent on shipped weight and as 40% of the weight of the sensor is water, the ability to test and ship empty sensors is significant.

From the preceding descriptions, it is important to note that the relative humidity inside the sensor cavity can be controlled by changing the thickness of the permeation barrier. Increasing the thickness of this barrier leads to a lower internal RH which results in a lower level of water loss from the sensor. The life expectancy of a sensor of this type is a function of the total volume of the water reservoir divided by the rate of water loss from the sensor. There is a strong imperative to get the maximum life out of the smallest sensor, which means reducing the rate of sensor water loss as much as possible.

To this end it is desirable to be able to operate the sensor with as low a level of internal RH as can be tolerated. The consequence of this is that the internal RH of the sensor becomes a stronger function of the external ambient RH, rendering the sensor CO sensitivity a function of external RH. In other words, as the internal RH of the sensor decreases, so does the sensitivity of the sensor to CO thereby making the sensor less effective. Although this loss of sensor CO sensitivity may be small enough such that compensation is not needed, it would be desirable to be able to adjust for this variation if necessary.

The reduction in internal RH within the sensor has the effect of reducing the water content of the MEA and this has a number of measurable consequences beyond the CO sensitivity shift. Two parameters that show a significant shift as the MEA dries are the sensor series resistance and the electrode bi-layer capacitance. The bi-layer capacitance is due to the thin film of water that develops on the surface of the grains of the electrode material, the more water, the greater the surface area of covered catalyst and the greater the capacitance. The change in resistance comes about because the ability of the NAFION part of the MEA to conduct protons (and inhibit electron conduction) is highly dependent on the water content of the NAFION. Protons pass through the NAFION layer as hydronium ions, that is, a proton bound to a water molecule and the water content of the NAFION directly controls the rate of proton transfer. Water content has a secondary effect on NAFION conduction. That is, in order for hydrogen ions to pass through the NAFION layer, they must be surrounded by water molecules to form hydronium ions. Under very low humidity conditions, the NAFION layer will dry up and shrink, and this will cause shrinkage of the conducting channels within the mass of the NAFION layer. This produces a further restriction on the transport of protons in that it is now more difficult for hydronium ions to pass through the NAFION layer. Experiments carried out to date have shown that the capacitance variation is the strongest, with values ranging from typically 8 mF when completely hydrated to below 4 mF when dry. The resistance shift is more difficult to measure but is typically 3 Ohms to 10 Ohms over the same humidity range.

The magnitude of CO sensitivity loss, when operating at low levels of ambient humidity, that is the RH level of the environment around the sensor, is about 30% for ambient RH levels down to about 15% RH. At a lower level, such as 5% RH, the CO sensitivity loss can reach 50%. In reality, a variation in sensor sensitivity of about 30% would be acceptable for a detector to be used in a home environment. UL standard 2034 only requires operation of such sensors down to an ambient RH level of 15%. The time taken for the MEA in a sensor to lose water when exposed to low humidity ambient environments is typically a week or more. As a result, if the present sensor is operating in low humidity ambient environments, a check on the sensor resistance and/or capacitance would be necessary perhaps every 24 hours if the sensor is to be adjusted for low ambient humidity.

Measurement of both series resistance and capacitance of a sensor in-situ in a detector is comparatively straightforward and so it is possible to produce a sensor, with a very low rate of water loss for its sensitivity and size, that requires active correction of the sensor CO sensitivity using real time measurements of sensor resistance and/or capacitance. In other words, the sensor could be adjusted in use to compensate for humidity changes. Humidity compensation is not a process that occurs within the sensor, instead, it is implemented by the microprocessor/controller 37 that controls the entire CO detector system. The resistance and/or capacitance of the sensor 10 is dependent on the water content of the MEA, which, in turn, is dependent on the level of RH within the sensor.

The resistance of a sensor can be measured by passing a very low level AC current (less than 10 microamps) through the sensor at a frequency of typically about 500 Hz and measuring the voltage developed across the sensor. The current would be derived from the microprocessor/controller 37 that controls the CO sensor 10 by, for example, connecting one of the digital output ports of the microprocessor to the working electrode 18A of the sensor 10 via a high value resistor (>100 kOhms). The resistance measurement process takes typically 2 seconds and is thus a quick process. In contrast, to measure the capacitance, the applied frequency must be about 0.5 Hz or lower, producing a measurement time of probably about 10 seconds, still not unduly long, but probably longer than would be desirable.

When a CO detector is first assembled, it is calibrated. Since the output of every CO sensor is slightly different, the calibration process places the detector in a known concentration of CO (typically about 150 ppm) and measures the sensor output. This measured output value is then stored within the memory of the microprocessor such as microprocessor/controller 37 illustrated in FIG. 2 and is used to scale the output of the sensor detector in real world operation. That is, if the detector subsequently sees a sensor output that is half of its memorized value, the detector interprets that as a CO concentration of 75 ppm. In order to compensate for variations in the ambient environment such as temperature or humidity, a calibration constant is determined during calibration for a predetermined set of parameters such as at known internal RH values and/or known external RH values or other conditions, and the memorized calibration constant is adjusted by a predetermined amount, depending on the ambient conditions. In order to be able to do this the manufacturer needs to know how the sensor output and/or the CO sensitivity of the sensor varies with ambient conditions. All of this information can be obtained prior to the sensor being used in a detector product by conducting different sensor resistance and/or capacitance measurements at different internal and/or external RHs of the sensor. Adjustment and/or correction factors can likewise be determined for correcting or adjusting a known calibration constant. Look-up tables can be developed correlating different sensor resistance and/or capacitance to different internal and external RHs and to an adjustment value for correcting the calibration constant.

Temperature compensation is used in almost all CO detectors from any manufacturer, either using a thermistor (a resistor that changes its resistance as a function of temperature), or sometimes some property of the microprocessor is temperature sensitive. Humidity compensation is almost never used because there is no such thing as a reliable, low cost humidity sensor. The present method replaces the need for a humidity sensor, with the ability of the microprocessor/controller 37 to measure the change in water concentration of the MEA by measuring the resistance and/or capacitance of the sensor 10 and using this value through, for example, look-up tables, to control the modification of the calibration constant. The periodic check on sensor resistance and/or capacitance can be performed by and programmed into the microprocessor/controller 37 controlling the operation of the entire sensor/detector system. The above referenced look-up tables can likewise be stored or programmed into the microprocessor/controller 37 and the controller can automatically control the adjustment of the calibration constant to compensate for the current humidity conditions so as to keep the CO sensitivity loss within a pre-determined range.

It is also recognized and anticipated that the calibration of the present sensor 10 can take on many different methods and approaches as compared to the approach discussed above in order to compensate for changes in the current humidity conditions in which the sensor 10 will operate. For example, the present sensor can be calibrated at a plurality of different internal relative humidities of the sensor (ion conducting solid electrolyte membrane) and/or at a plurality of different ambient external relative humidities of the sensor and a calibration constant can be established for each of the different internal and external relative humidities.

Each of the different internal and external relative humidities of the sensor can then be correlated to a sensor output and each calibration constant can be correlated to a sensor output indicative of a concentration of a gas based upon the internal and external relative humidities of the sensor. In addition, the resistance and/or capacitance of the sensor can be measured and these measurements likewise correlated to the internal and/or external relative humidity of the sensor. A controller can be programmed to periodically check the resistance and/or capacitance of the sensor and then correlate the sensor resistance and/or capacitance measured to either the internal and/or external relative humidity of the sensor. The controller can then automatically adjust the appropriate calibration constant based upon the measured sensor resistance and/or capacitance so as to compensate for the current internal and/or external humidity conditions of the sensor.

Still further, testing and/or calibration of the sensor to achieve compensation for current humidity conditions can be accomplished by simply measuring the resistance and/or capacitance of the sensor at a plurality of different internal and/or external relative humidities of the sensor; storing the measured sensor resistance and/or capacitance in the memory of a controller; exposing the sensor to a predetermined concentration level of a gas; calibrating the sensor output at a predetermined internal and/or external relative humidity of the sensor based upon the predetermined concentration level of a gas exposed to the sensor; correlating the sensor output to the concentration level of a gas; determining a calibration constant for the sensor output at the predetermined internal and/or external relative humidity of the sensor; programming the controller so as to periodically check the resistance and/or capacitance of the sensor and to correlate such measurements to the internal and external relative humidity of the sensor; and then having the controller automatically adjust the calibration constant to compensate for the current humidity conditions of the sensor.

Still further, the present sensor can be calibrated to yield a calibration constant which is correlated to the output of the sensor, which output is indicative of a concentration level of a particular gas such as carbon monoxide measured by the sensor at a certain predetermined internal relative humidity of the sensor, programming a controller to periodically measure the resistance and/or capacitance of the sensor to determine the current internal relative humidity of the sensor; and then having the controller adjust the calibration constant to compensate for the current internal relative humidity condition of the sensor.

Still further, a method for compensating for changes in relative humidity of the sensor can be accomplished by determining the sensor output at a known relative humidity condition; calibrating the sensor output at the known relative humidity condition to a concentration level of the gas measured by the sensor; determining a calibration constant based upon the sensor output at the known relative humidity condition; measuring the resistance and/or capacitance of the sensor and correlating such measurements to the relative humidity condition of the sensor; periodically adjusting the calibration constant based upon the current measurement of the resistance and/or capacitance of the sensor to compensate for different relative humidity conditions. In this scenario, the relative humidity conditions of the sensor can be either the internal relative humidity of the ion conducting solid electrolyte membrane, or it can be the external ambient relative humidity of the environment in which the sensor is operating. Still other methods for adjusting the present sensor in-situ due to changes in the current humidity conditions of the sensor so as to keep the gas sensitivity loss within a predetermined range are also recognized and anticipated.

It is also recognized and anticipated that the overall dimensions of the present sensor 10 as well as the specific shape and configuration of the various components associated therewith as set forth in FIG. 1 are subject to wide variations and all such components may be sized and shaped into a wide variety of different sizes and configurations so as to be compatible with the size and shape associated with a particular application without impairing the teachings and practice of the present invention. Other variations and modifications to the various components comprising the present sensor 10 as illustrated in FIGS. 1-9 are also contemplated.

Thus, there has been shown and described a novel carbon monoxide sensor system which is adapted for installation into a total detector system which includes a warning system, which sensor system fulfills all of the objects and advantages sought therefor. Many changes, modifications, variations, and other uses in applications of the present invention will, however, become apparent to those skilled in the art after considering this specification and the accompanying drawings. All such drawings, modifications, variations and other uses in applications which do not depart from the spirit and scope of the present invention are deemed to be covered by the present invention which is limited only by the claims which follow.

The invention claimed is:

1. A gas sensor comprising:
   an ion conducting solid electrolyte membrane having opposed side portions;
   a first working electrode positioned adjacent one opposed side portion of said solid electrolyte membrane;
   a second counter electrode positioned adjacent the other opposed side portion of said solid electrolyte membrane wherein an electrical signal is produced between said first and second electrodes in response to the presence of a gas at the first electrode;
   a water reservoir for providing a water vapor source to said ion conducting solid electrolyte membrane;
   a water permeation barrier positioned adjacent said water reservoir, said water permeation barrier being comprised of a material that is non-porous, electrically non-conductive, permeable to water vapor and impermeable to at least carbon monoxide, said water permeation barrier separating the ion conducting solid electrolyte membrane from said water reservoir; and
   a housing member for holding said first and second electrodes and said ion conducting solid electrolyte membrane, said housing member including said water permeation barrier.

2. The gas sensor defined in claim 1 wherein said water permeation barrier is a solid thin walled member having opposed surfaces and wherein the water vapor passes through one of the opposed surfaces of said thin walled member, diffuses therethrough, and evaporates from the opposite surface thereof.

3. The gas sensor defined in claim 1 wherein said water permeation barrier is made from a polycarbonate material having a thickness in the range of about 0.01 inches to about 0.03 inches.

4. The gas sensor defined in claim 1 including an electrically conductive gas diffusion layer positioned in contact with said second counter electrode, said gas diffusion layer separating said second counter electrode from said water permeation barrier.

5. The gas sensor defined in claim 4 wherein said gas diffusion layer includes an opening extending therethrough for allowing water vapor to pass therethrough.

6. The gas sensor defined in claim 4 including an electrically conductive gas diffusion layer positioned in contact with said first working electrode.

7. The gas sensor defined in claim 6 including a gas entry passageway for allowing a gas in an ambient environment to enter the sensor, said gas diffusion layer positioned in contact with said front working electrode including an opening extending therethrough, said opening being in communication with said gas entry passageway for allowing a gas to pass therethrough to said first working electrode.

8. The gas sensor defined in claim 7 including a first conductive electrode contact member positioned in direct contact with the gas diffusion layer positioned in contact with said first working electrode, and a first housing member having a groove formed in a surface thereof, said gas entry passageway being formed when said first electrode contact member is mated with said first housing member and overlays said groove, said first housing member including an opening extending therethrough in communication with said groove for allowing a gas to enter said first housing member, said first electrode contact member including an opening extending therethrough in communication with said groove for allowing a gas to exit said gas entry passageway.

9. The gas sensor defined in claim 8 wherein said first housing member includes a recess for receiving a filter.

10. The gas sensor defined in claim 1 wherein said housing member includes a shoulder portion and a reinforcement disc positionable on said shoulder portion and overlaying said water permeation barrier for protecting said water permeation barrier, said reinforcement disc including an opening extending therethrough for allowing water vapor to pass therethrough.

11. The gas sensor defined in claim 4 including a second conductive electrode contact member positioned in direct contact with the gas diffusion layer positioned in contact with said second counter electrode.

12. The gas sensor defined in claim 11 including an electrically conductive resilient member positioned between the gas diffusion layer positioned in contact with said second counter electrode and said second electrode contact member, said electrically conductive resilient member including an opening extending therethrough for allowing water vapor to pass therethrough.

13. The gas sensor defined in claim 8 wherein said groove has a depth of about 0.25 mm and a width of about 0.25 mm.

14. The gas sensor defined in claim 8 including a second housing member mateable with said first housing member, said second housing member including said water permeation barrier.

15. The gas sensor defined in claim 14 wherein said water reservoir is associated with a third housing member, said third housing member being over-molded around at least a portion of said first and second housing members so as to enclose at least a portion of said first and second housing members within said third housing member.

16. The gas sensor defined in claim 1 wherein the sensor is coupled to a controller and wherein the sensor is calibrated to yield a calibration constant which is correlated to the output of the sensor, said sensor output being indicative of a concentration level of a gas measured by the sensor at a certain predetermined internal relative humidity of the sensor, said controller being programmed to periodically measure the resistance and/or capacitance of the sensor to determine the current internal relative humidity of the sensor, and said controller being programmed to adjust the calibration constant to compensate for the current internal relative humidity condition of the sensor.

17. A gas sensor comprising:
a first working electrode and a second counter electrode;
an ion conducting solid electrolyte membrane positioned between said first and second electrodes wherein an electrical signal is produced between said first and second electrodes in response to the presence of a gas at the first working electrode;
a first housing member having a groove formed therein, said groove being positioned and located so as to face said first working electrode, said first housing member having a hole extending therethrough in communication with said groove for allowing an ambient gas to enter said groove; and
a second member overlaying said groove and forming a gas entry passageway therebetween, said second member having an opening extending therethrough in communication with said groove for allowing an ambient gas to flow therethrough.

18. A method for constructing and assembling a gas entry passageway for a gas sensor having first and second working and counter electrodes, and an ion conducting solid electrolyte membrane positioned between said first and second electrodes, the gas entry passageway allowing a gas from the ambient environment to migrate to the first working electrode, said method comprising:
providing a first member having first and second opposed surfaces and an opening extending therethrough;
forming a groove on one of the first and second surfaces of said first member, said groove running in the plane of said first or second surface and being in communication with said opening;
providing a second member having first and second opposed surfaces and an opening extending therethrough;
mating said second member with said first member such that one of the first and second surfaces of said second member overlays the groove formed in one of the first and second surfaces of said first member;
positioning and locating the opening extending through said second member so as to be in communication with the groove of said first member when said first and second members are mated together, the mating of said first and second members forming the gas entry passageway associated with said sensor, the gas entry passageway allowing a gas from the ambient environment to pass through the opening associated with said first member, through the groove formed in said first member, and through the opening formed in said second member en route to the first working electrode.

19. The method defined in claim 18 wherein said second member is an electrode contact member which is electrically coupled to said first working electrode, said electrode contact member electrically connecting the sensor to an external circuit.

20. The method defined in claim 19 including:
providing an electrically conducting gas diffusion layer between said electrode contact member and said first working electrode, said gas diffusion layer electrically coupling said electrode contact member to said first working electrode.

21. A method of assembling a gas sensor having first and second working and counter electrodes, an ion conducting solid electrolyte membrane positioned between said first and second electrodes, first and second electrically conducting gas diffusion layers positioned respectively adjacent said first and second electrodes, first and second electrode contact members positioned respectively adjacent said first and second gas diffusion layers, and first and second housing members, the method of assembly comprising:
positioning said first and second electrode contact plates, said first and second gas diffusion layers, said first and second electrodes, and the ion conducting solid electrolyte membrane between said first and second housing members thereby forming a sub-assembly;
placing the sub-assembly into a molding machine and over-molding thereto a third housing member having a water reservoir associated therewith, the over-molding process forming a wall portion around the sub-assembly enclosing at least a portion of the sub-assembly within said third housing member.

22. The method defined in claim 21 wherein said overmolding process produces a continuous housing member enclosing at least a side wall portion of said sub-assembly.

23. The method defined in claim 21 wherein said overmolding process is conducted at a temperature which is sufficient to at least partially melt a projecting rib extending around the perimeter of the second housing member to a corresponding flange extending around the perimeter of said first housing member.

24. The method defined in claim 21 including forming a thin walled water permeation barrier within said second housing member, said water permeation barrier extending over the water reservoir formed in said third housing member.

* * * * *